United States Patent
Han et al.

(10) Patent No.: US 12,102,443 B2
(45) Date of Patent: Oct. 1, 2024

(54) DEVICE FOR MEASURING TRANSEPIDERMAL WATER LOSS AND SKIN CARE SYSTEM USING SAME

(71) Applicant: GPOWER INC., Seoul (KR)

(72) Inventors: Chang Hee Han, Gyeonggi-do (KR); Deug Ki Lee, Seoul (KR)

(73) Assignee: GPOWER INC., Seoul (KR)

(*) Notice: Subject to any disclaimer, the term of this patent is extended or adjusted under 35 U.S.C. 154(b) by 1125 days.

(21) Appl. No.: 16/318,243

(22) PCT Filed: Jul. 18, 2017

(86) PCT No.: PCT/KR2017/007683
§ 371 (c)(1),
(2) Date: Jan. 16, 2019

(87) PCT Pub. No.: WO2018/016834
PCT Pub. Date: Jan. 25, 2018

(65) Prior Publication Data
US 2019/0167184 A1    Jun. 6, 2019

(30) Foreign Application Priority Data

Jul. 18, 2016 (KR) .................. 10-2016-0090753
Jul. 18, 2016 (KR) .................. 10-2016-0090755

(51) Int. Cl.
*A61B 5/00* (2006.01)
*A61Q 19/00* (2006.01)
(Continued)

(52) U.S. Cl.
CPC ............ *A61B 5/443* (2013.01); *A61Q 19/007* (2013.01); *G01N 15/0826* (2013.01);
(Continued)

(58) Field of Classification Search
CPC ... A61B 5/443; A61B 5/442; A61B 2562/029; A61B 5/11; A61B 5/721;
(Continued)

(56) References Cited

U.S. PATENT DOCUMENTS

2005/0188747 A1* 9/2005 Kellerman ............ G01N 25/56
                                                                73/29.01
2006/0243048 A1* 11/2006 Imhof .................... G01N 25/56
                                                                374/142
(Continued)

FOREIGN PATENT DOCUMENTS

JP          05-003857 A       1/1993
JP          2003-339647 A    12/2003
(Continued)

OTHER PUBLICATIONS

English Machine Translation of JP-2012085983 (Year: 2012).*
International Search Report for PCT/KR2017/007683 mailed on Nov. 13, 2017.

*Primary Examiner* — Yi-Shan Yang
*Assistant Examiner* — Kyle W. Kretzer
(74) *Attorney, Agent, or Firm* — The PL Law Group, PLLC

(57) ABSTRACT

A transepidermal water loss measurement device includes a cylindrical closed chamber having a closed end and an open end to come into contact with the skin at a position at which a rate of water loss is to be measured and a transepidermal water loss measurement unit that measures a rate of transepidermal water loss of the skin by detecting levels of humidity and changes in humidity level in the closed chamber.

13 Claims, 5 Drawing Sheets

(51) Int. Cl.
*G01N 15/08* (2006.01)
*G01N 25/56* (2006.01)
*G01N 33/483* (2006.01)
*G01N 7/14* (2006.01)

(52) U.S. Cl.
CPC .......... *G01N 33/4833* (2013.01); *A61B 5/442* (2013.01); *A61B 2562/029* (2013.01); *G01N 7/14* (2013.01); *G01N 2015/086* (2013.01); *G01N 25/56* (2013.01)

(58) Field of Classification Search
CPC .......... A61B 2562/0219; A61Q 19/007; G01N 15/0826; G01N 33/4833; G01N 7/14; G01N 25/56; G01N 2015/086
See application file for complete search history.

(56) References Cited

U.S. PATENT DOCUMENTS

| | | | | |
|---|---|---|---|---|
| 2015/0045631 | A1* | 2/2015 | Ademola | A61B 5/443 600/301 |
| 2016/0022209 | A1* | 1/2016 | Fraisl | A63B 24/0062 600/590 |
| 2016/0157732 | A1* | 6/2016 | Tanaka | G01J 5/026 600/474 |

FOREIGN PATENT DOCUMENTS

| | | | |
|---|---|---|---|
| JP | 2012085983 A | * | 5/2012 |
| JP | 2015-029881 A | | 2/2015 |
| KR | 10-2015-0105574 A | | 9/2015 |
| KR | 10-2015-0135142 A | | 12/2015 |

* cited by examiner

DEVICE FOR MEASURING TRANSEPIDERMAL WATER LOSS AND SKIN CARE SYSTEM USING SAME

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2017/007683, filed on Jul. 18, 2017, which claims priority to the benefit of Korean Patent Application No. 10-2016-0090753 filed on Jul. 18, 2016 and 10-2016-0090755 filed on Jul. 18, 2016 in the Korean Intellectual Property Office, the entire contents of which are incorporated herein by reference.

TECHNICAL FIELD

The present invention relates to a device for measuring and managing transepidermal water loss (TEWL). More particularly, the present invention relates to a transepidermal water loss measurement device and a skin care system using the same, the device and system being capable of automatically correcting measured rates of transepidermal water loss according to an inclination angle of a closed chamber at the time of measuring the transepidermal water loss, thereby preventing occurrence of a measurement error attributable to a pressure change in the closed chamber, and correcting the measured results at various inclination or measurement angles to improve the accuracy and reliability of the measured results. In addition, the device and system prevents a rapid change in the internal pressure of the closed chamber due to heat and vapor generated from the skin during the measurement of the transepidermal water loss, thereby improving the accuracy and reliability of the measured results. In addition, the device and system share the measured results so that skin barrier function can be effectively monitored and managed.

BACKGROUND ART

The skin is the outermost part of the human body and performs important functions such as prevention of intrusion of bacteria and harmful substances into the interior of the human body from outside, waterproofing, and temperature control. This function is called skin barrier function, and the rate of transepidermal water loss (TEWL) is a representative index of the skin barrier function.

In the case where the skin barrier function is deteriorated, that is, when the rate of the transepidermal water loss is high, external allergens easily permeate into the skin and various skin diseases such as atopic symptoms occur. Therefore, strengthening and maintaining the skin barrier function is important especially for skin disease patients. The prevalence of atopy is high in newborns with a high rate of transepidermal water loss, and the prevalence can be halved by proper moisturizing control.

Stratum corneum hydration (SCH), which is the amount of water the skin is holding, is about 20 to 70%. On the other hand, the atmospheric air adjacent to the skin surface is lower in water content than the skin. Therefore, the water inside the stratum corneum (SC) evaporates and diffuses into the surrounding atmosphere. Conventionally, transepidermal water loss (TEWL) was measured by placing an open chamber or a closed chamber on the skin and monitoring changes in the humidity in the chamber. In this regard, it is known that the measurement accuracy of the closed chamber is higher than that of the open chamber. Therefore, the closed chamber is currently dominantly utilized. As such, when a closed chamber is placed so as to cover a certain area of the skin, the skin moisture evaporates and diffuses into the atmospheric air existing in the closed chamber. At this time, an increase rate of the humidity in the chamber is measured to detect the transepidermal water loss.

However, conventional transepidermal water loss measurement methods have a problem that the reliability of measured results deteriorates because the internal pressure of the closed chamber fluctuates with external factors.

Specifically, since the body temperature or the skin temperature of a person is generally higher than the ambient atmospheric temperature, when a closed chamber is placed to cover a certain area of the skin in order to measure the transepidermal water loss, the internal temperature of the closed chamber is likely to rise. As the internal temperature of the closed chamber rises, a measurement environment accordingly changes. For example, the internal pressure of the closed chamber increases. As a result, the humidity and the transepidermal water loss measured at this time are likely to have a high error rate and poor accuracy.

In the past, there was an attempt to solve such a problem by training general users or skilled experts to properly use measurement devices. However, this training method was not convenient or effective for general users. Therefore, a more effective solution than the training method is required.

SUMMARY

Accordingly, the present invention has been made in view of the problems described above and an objective of the present invention is to provide a transepidermal water loss measurement device and a skin care system using the same, the device and system being capable of automatically correcting measured results according to an inclination of the measurement device at the time of measuring a transepidermal water loss and of preventing a rapid change in internal pressure of a closed chamber by the skin temperature, thereby improving the measurement accuracy and the reliability of measured results.

Technical Solution

In order to accomplish the objective of the present invention, according to one aspect of the present invention, there is provided a transepidermal water loss measurement device including: a one-end closed cylindrical chamber having a closed end and an open end which comes into contact with a region of the skin; and a transepidermal water loss measurement unit that measures a transepidermal water loss of the skin by detecting a humidity and a humidity change inside the closed chamber.

The transepidermal water loss measurement unit detects the humidity and an inclination or measurement angle of the closed chamber during measurement of the humidity and performs self-calibration to compensate for an error of measurements attributable to the inclination or measurement angle of the closed chamber, thereby outputting corrected measurement results of the transepidermal water loss according to the inclination or measurement angle of the closed chamber.

The closed chamber may be provided with a pressure-adjusting ventilation unit having a predetermined area (two-dimensional size) and thickness on an outer wall surface of the closed chamber to adjust a pressure gradient and a density gradient inside the closed chamber in accordance with a pressure difference and a density difference between an inside space and an outside space of the closed chamber.

According to another aspect of the present invention, there is provided a skin care system using a transepidermal water loss measurement device. The system includes a transepidermal water loss measurement device and at least one mobile communication device that receives transepidermal water loss information from the transepidermal water loss measurement device through a short-range wireless communication network and displays the transepidermal water loss information as a numerical value by executing an application program such that the user of the measurement device can recognize the transepidermal water loss information.

As described above, the transepidermal water loss measurement device and the skin care system using the same, according to the present invention, automatically compensate for the errors in measurements according to an inclination angle at a specific point in time or an average inclination angle during the measurement of transepidermal water loss, thereby preventing the errors in the measurements, which are attributable to fluctuations in measurement conditions, and improving the measurement accuracy and the reliability of the measured results even at various inclination or measurement angles of the closed chamber.

In addition, it is possible to prevent a rapid change in the internal pressure of the closed chamber, which is primarily influenced by the skin temperature, during the measurement of the skin moisture, thereby improving the measurement accuracy and reliability of the measured results.

In addition, the transepidermal water loss measurement device and the user mobile communication device are configured to interwork with a management server to share accurate and reliable measurements and to effectively care for the skin according to the measured results.

DETAILED DESCRIPTION

Hereinafter, exemplary embodiments of the present invention will be described in detail with reference to the accompanying drawings.

Figure 1:
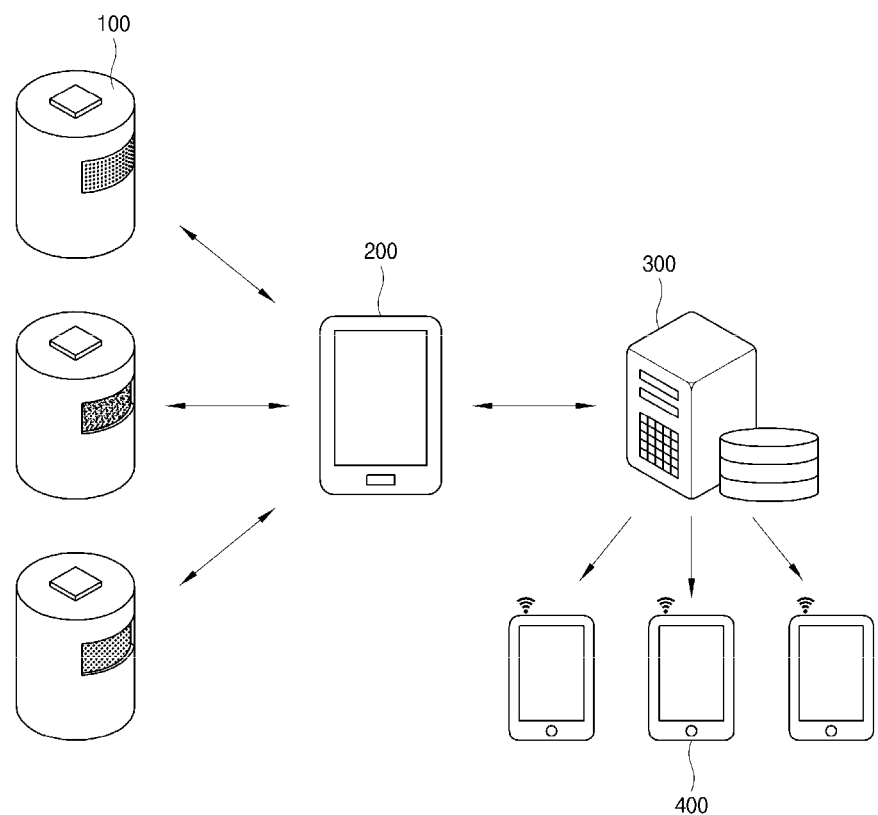
FIG. 1 is a block diagram illustrating the configuration of a transepidermal water loss measurement device according to one embodiment of the present invention and the configuration of a skin care system using the transepidermal water loss measurement device.

FIG. 1 is a block diagram illustrating the configuration of a transepidermal water loss measurement device according to one embodiment of the present invention and the configuration of a skin care system using the transepidermal water loss measurement device.

As illustrated in FIG. 1, according to one embodiment of the present invention, a transepidermal water loss measurement device 100 is of a closed cylindrical chamber type in which one end of a cylindrical chamber is open so as to come into contact with the skin at a position at which the transepidermal water loss is to be measured and the opposite end of the cylindrical chamber is closed. The rate of the transepidermal water loss is measured by detecting and analyzing the humidity inside the closed chamber and the amount of water evaporating from the skin surface being in contact with the open end of the closed chamber.

The water content (i.e., skin hydration) in the stratum corneum is about 20 to 70% and is higher than that of the atmospheric air adjacent to the skin surface. Therefore, the water contained in the stratum corneum evaporates and diffuses into the atmospheric air from the skin surface. Accordingly, when the open end of the closed-chamber of the transepidermal water loss measurement device 100 is placed on a part of the skin to measure the water loss from the skin surface, the moisture evaporates and diffuses into the air trapped in the closed-chamber of the transepidermal water loss measurement device 100. At this time, the increase rate of the humidity in the chamber is detected to measure the transepidermal water loss.

The transepidermal water loss measurement device 100 corrects the measured value of transepidermal water loss according to an inclination or measurement angle of the closed chamber at the time of detecting the humidity and the amount of water evaporating from the skin surface, and outputs the corrected value. When a part of the skin is covered by the closed-chamber of the transepidermal water loss measurement device 100, a convection phenomenon occurs in which low density air containing a large amount of moisture heated by the skin temperature rises inside the closed chamber. Therefore, the error rates of the humidity and the transepidermal water loss that are measured increase with the inclination or measurement angle of the closed chamber. In order to prevent such a measurement error, that is, in order to reduce an error rate, the inclination of the closed chamber is also measured during the measurement of the humidity and the amount of water evaporating from the skin surface, and the measured value of transepidermal water loss is corrected according to the inclination of the closed chamber.

When a part of the skin is covered by the closed-chamber of the transepidermal water loss measurement device 100, the internal temperature of the closed chamber increases due to the high skin temperature, resulting in an increase in the internal pressure of the closed chamber and a decrease in the air density in the closed chamber. In other words, since the skin temperature is higher than the ambient air temperature, when the closed chamber is placed to cover the skin, the internal temperature and the internal pressure of the closed chamber rise and the density inside the chamber decreases. According to the ideal gas law (called general gas equation, PV=nRT), when the internal temperature of the chamber increases, since the volume of the closed chamber is constant, the internal pressure of the chamber increases. As the internal pressure increases, the evaporation rate of water from the skin surface decreases. That is, since the measurement conditions such as the internal pressure at the time of measuring the water loss fluctuate with external factors, a measurement error is likely to occur. In order to prevent the occurrence of such a measurement error, at least a part of the outer wall surface of the transepidermal water loss measurement device 100 is provided with a pressure-adjusting ventilation unit having a predetermined area (two-dimensional size) and thickness. The pressure-adjusting ventilation unit adjusts the pressure gradient in the closed chamber according to a difference between the internal pressure and the external pressure of the closed chamber.

The opposite end (closed end) of the closed chamber of the transepidermal water loss measurement device 100 is provided with a water content measurement unit for measuring the water content in the skin surface (i.e., stratum corneum hydration (SCH)) and the water loss (i.e., the transepidermal water loss) from the skin surface. The water content measurement unit accurately measures the water content (SCH) and the water loss (transepidermal water loss) in a state in which a pressure difference and a density difference between the inside and the outside of the closed chamber are reduced. The measured rate of transepidermal water loss is transmitted as transmission data through a short-range or long-range wireless communication network so that the user can share and check information on the transepidermal water loss in the form of quantized data by using a mobile communication device such as a smart phone. Meanwhile, the data of the transepidermal water loss information can be managed by a management server so as to be shared by interested parties. The user can be provided with a user-specific skin caring method according to the measured transepidermal water loss and other related information through a mobile communication device such as a smart phone.

Figure 2:
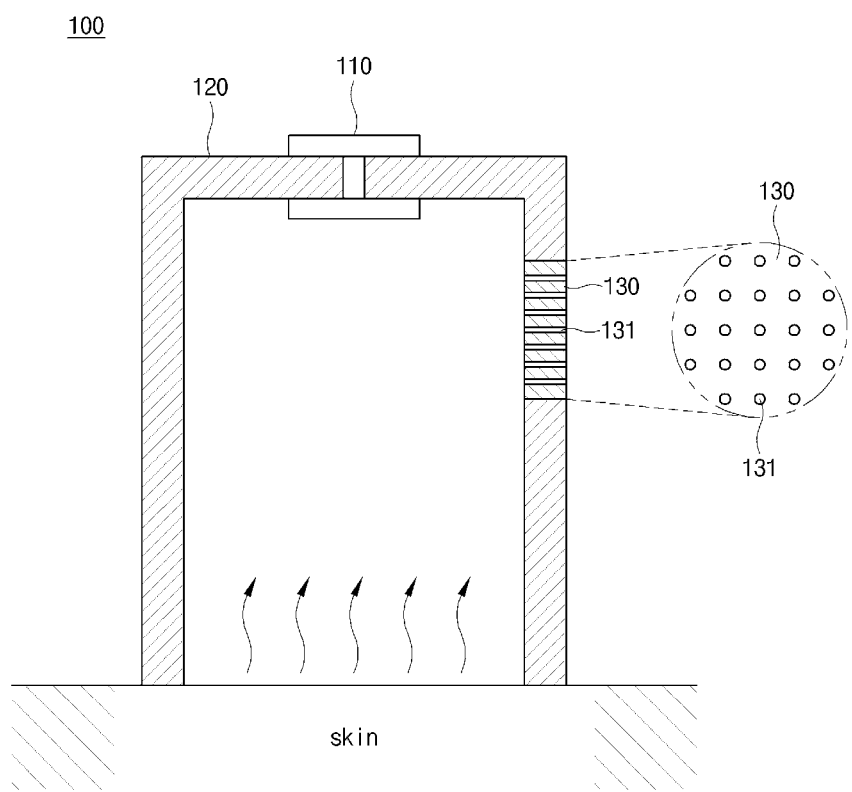
FIG. 2 is a diagram illustrating the detailed configuration of the transepidermal water loss measurement device of FIG. 1.

FIG. 2 is a diagram illustrating the detailed configuration of the transepidermal water loss measurement device of FIG. 1.

Referring to FIG. 2, the transepidermal water loss measurement device 100 includes the cylindrical closed chamber 120, the pressure-adjusting ventilation unit 130, and the water content measurement unit 110. The cylindrical closed chamber 120 has an open end to come into contact with a part of the skin to measure the water loss from the part of the skin, and a closed end. The pressure-adjusting ventilation unit 130 adjusts the pressure and density gradients inside the closed chamber 120 according to the differences in pressure and density between the inside and the outside of the closed chamber 120. The water content measurement unit 110 detects the humidity in the closed chamber and measures the transepidermal water loss on the basis of information of the detected humidity.

The transepidermal water loss measurement unit 110 is provided at the closed end of the closed chamber 120. The water content measurement unit 110 is provided in the closed chamber 120 and is configured to passes out through the closed end from the inside of the closed chamber 120.

The transepidermal water loss measurement unit 110 measures and analyzes the transepidermal water loss by detecting the humidity and the changes in the humidity in the closed chamber 120 during the measurement of the transepidermal water loss. The transepidermal water loss measurement unit 110 performs self-calibration on the basis of the measured rates of transepidermal water loss according to the inclination or measurement angle of the closed chamber at the time of detecting the humidity, converts the resulting water loss as data, and displays the data on a display unit. In addition, the transepidermal water loss measurement unit 110 transmits the data of the transepidermal water loss information corrected through the self-calibration to an external device through a wireless communication network so that the data of the transepidermal water loss information can be shared by interested parties.

The pressure-adjusting ventilation unit 130 is provided in a region of the wall of the closed chamber and is configured to have a predetermined area (two-dimensional size) and thickness. The pressure-adjusting ventilation unit 130 has a thin film shape having a thickness equal to or smaller than that of the wall of the closed chamber 120. The pressure-adjusting ventilation unit 130 is provided with one or more ventilation holes 131 that are arranged regularly or irregularly and have an inner diameter that is $\frac{1}{1000}$ times the total surface area of the closed chamber 120 or the total surface area of the pressure-adjusting ventilation unit 130.

When the pressure-adjusting ventilation unit 130 has a thin film shape and is provided with the multiple ventilation holes 131 having an inner diameter that is $\frac{1}{1000}$ times the total surface area of the pressure-adjusting ventilation unit 130, the pressure gradient and the density gradient in the closed chamber can be adjusted according to a pressure difference and a density difference between the inside and the outside of the closed chamber 120.

Specifically, since the rate of increase in the partial pressure of water vapor resulting from water evaporation and the transfer rate of the pressure in the closed chamber 120 are faster than the vapor diffusion and convection caused by the high skin temperature, the air in the closed chamber 120 is exhausted through the ventilation holes 131, resulting in a constant pressure being maintained in the closed chamber 120. Assuming that the temperature rise during the measurement of transepidermal water loss is 1°, the volume increase and the pressure increase are each 0.33%. However, since the internal air is exhausted through the ventilation holes 131, a constant internal pressure can be maintained in the closed chamber. In this regard, since the pressure in the closed chamber 120 is always higher than the atmospheric pressure, the air flows from the inside to the outside of the closed chamber. Therefore, when the size of the open end and the size of the ventilation hole 131 are known, the amount of water evaporated and diffused into the air from the skin surface can be calculated.

Figure 3:
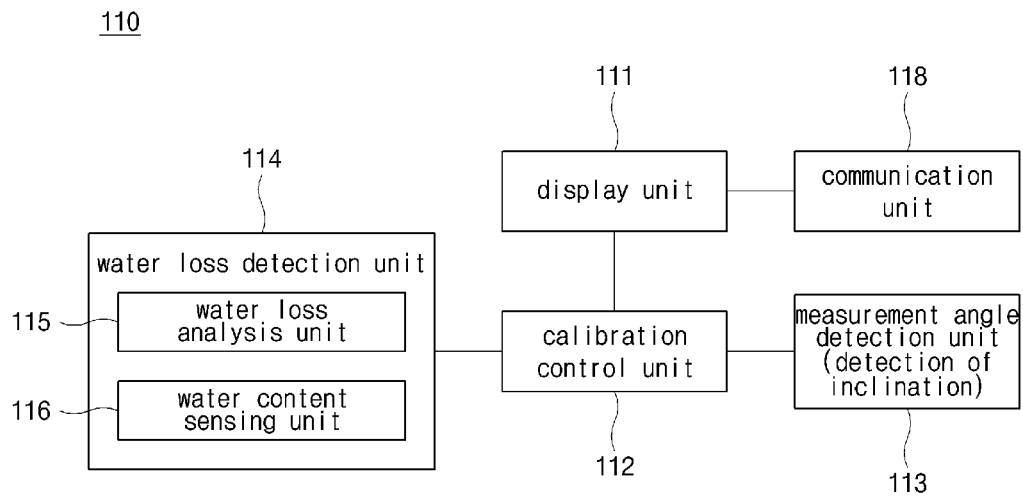
FIG. 3 is a block diagram illustrating the detailed configuration of a water content measurement unit of FIG. 2.

FIG. 3 is a block diagram illustrating the detailed configuration of the water content measurement unit of FIG. 2.

Referring to FIG. 3, the transepidermal water loss measurement unit 110 includes a water loss detection unit 114, a measurement angle detection unit 113, a calibration control unit 112, a display unit 111, and a communication unit 118.

Specifically, the water loss detection unit 114 detects the humidity and a change in the humidity in the closed chamber 120 at fixed intervals of time during the measurement of the transepidermal water loss and analyzes the changes in the humidity, thereby measuring the rates of the transepidermal water loss.

To this end, the water loss detection unit 114 includes: a water content sensing unit 116 including at least one humidity sensor or at least one moisture sensor and being configured to detect the humidity in the closed chamber 120 at fixed intervals of time during the measurement of the transepidermal water loss, and a water loss analysis unit 115 that receives the detected humidity in real time and analyzes the levels of humidity and the humidity changes at fixed intervals of time to calculate the rates of transepidermal water loss and subsequently converts the rates of the transepidermal water loss into data.

The measurement angle detection unit 113 includes at least one of an acceleration sensor, a gyro sensor, and a water droplet sensor capable of detecting an inclination or measurement angle of the closed chamber. The measurement angle detection unit 113 detects the inclination or measurement angle of the closed chamber 120 at fixed intervals of time during the detection of the humidity. The detected angle information is fed to the calibration control unit 112 that performs real-time calibration.

The measurement angle detection unit 113 measures the measurement angle by identifying the difference between the direction of the gravity and the axial direction of the closed chamber 120. In this case, the measurement angle detected by the measurement angle detection unit 113 includes an initial measurement angle that is an angle measured at the beginning of the measurement, an intermediate measurement angle that is an angle measured in the middle of the measurement, a final measurement angle that is an angle measured at the end of the measurement, all intermediate measurement angles that are angles measured multiple times during the measurement, and an average measurement angle over a measurement period.

The calibration control unit 112 corrects the measured rate of transepidermal water loss by performing numerical correction on the transepidermal water loss data detected by the water loss detection unit 114 according to the measurement angle information detected by the measurement angle detection unit 113.

The measurement angle information detected by the measurement angle detection unit 113 is at least any one of the initial measurement angle, the intermediate angle, the final measurement angle, all the intermediate measurement angles, and the average measurement angle. The calibration control unit 112 sets a predetermined threshold value corresponding to at least one of the initial measurement angle, the intermediate angle, the final measurement angle, all the intermediate measurement angles, and the average measurement angle, and add or subtracts the predetermined threshold value to or from the detected transepidermal water loss data, thereby correcting the numerical data of the transepidermal water loss. Here, the transepidermal water loss information which results from the numerical correction and the data conversion performed by the calibration control unit 112 is shared through the display unit 111 and the communication unit 118.

The display unit 111 includes a segment LED, a display panel, a flat panel display module and the like, and outputs (i.e., displays) the numerical data of the transepidermal water loss that results from the numerical correction and the data conversion performed by the calibration control unit 112. In addition, the display unit 111 displays the operation state of the calibration control unit 112, the communication state of the communication section 118, the power state, and the like.

The communication unit 118 transmits the transepidermal water loss information, which is data processed by the calibration control unit 112, to an external device through a wireless communication technique such as WiFi, Bluetooth, etc. Therefore, the data of the transepidermal water loss information can be shared.

Figure 4:
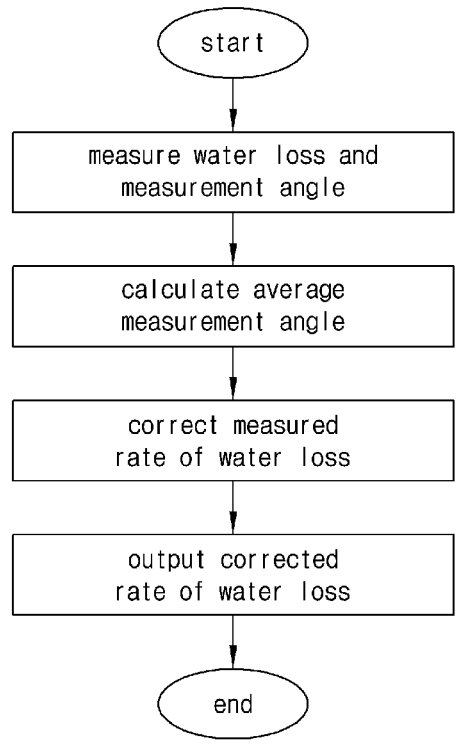
FIG. 4 is a flowchart illustrating a process of correcting the measured rate of water loss according to an inclination or measurement angle of the closed chamber and of outputting the corrected rate of water loss.

FIG. 4 is a flowchart illustrating a process of correcting the measured rate of water loss according to an inclination or measurement angle of the closed chamber and of outputting the corrected rate of water loss.

Referring to FIG. 4, the calibration control unit 112 of the transepidermal water loss measurement unit 110 receives the data of the transepidermal water loss information resulting from the analysis of the humidity changes performed by the water loss detection unit 114. The calibration control unit 112 receives angle information including at least one of the initial measurement angle, the intermediate angle, the final measurement angle, all the intermediate measurement angles, and the average measurement angle from the measurement angle detection unit 113.

Thus, the calibration control unit 112 corrects the numerical data of the transepidermal water loss by setting a predetermined threshold value corresponding to at least piece of the angle information among the initial measurement angle, the intermediate angle, the final measurement angle, all the intermediate measurement angles, and the average measurement angle and adds or subtracts the predetermined threshold value to or from the data of the transepidermal water loss. Here, the transepidermal water loss information which has undergone the numerical correction and the data conversion performed by the calibration control unit 112 is transferred to the display unit 111 and the communication unit 118 so as to be shared by interested parties.

Figure 5:
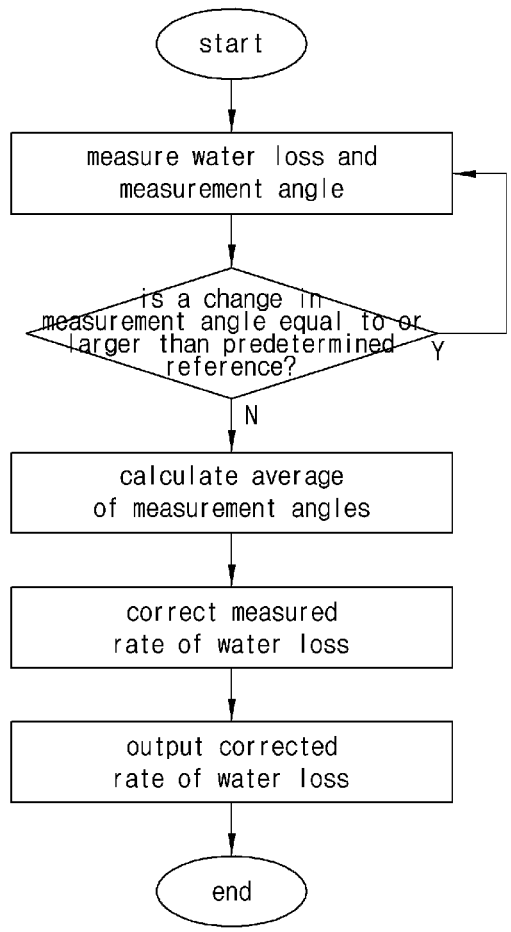
FIG. 5 is a flowchart illustrating a process of correcting a measured rate of water loss according to an inclination or measurement angle of the closed chamber and of outputting the corrected rate of water loss.

FIG. 5 is a flowchart illustrating a process of correcting a measured rate of water loss according to an inclination or measurement angle of the closed chamber and outputting the corrected rate of water loss.

Referring to FIG. 5, the calibration control unit 112 of the transepidermal water loss measurement unit 110 receives the data of the transepidermal water loss calculated through analysis of the humidity data from the water loss detection unit 114, and the angular information including the initial measurement angle, the intermediate angle, the final measurement angle, all the intermediate measurement angles, and the average measurement angle from the measurement angle detection unit 113.

Next, the calibration control unit 112 determines whether or not the closed chamber is moved by a predetermined reference angle or more during the measurement. When it is determined that the closed chamber is moved by the predetermined reference angle or more during the measurement, the user enters a command input to request repeating analysis of the humidity change, thereby measuring again the transepidermal water loss, the initial measurement angle, the intermediate angle, the final measurement angle, all the intermediate measurement angles, and the average measurement angle.

Conversely, when it is determined that the closed chamber is moved by less than the predetermined reference angle during the measurement, a predetermined threshold value corresponding to at least one (for example, the average measurement angle during the measurement period) of the initial measurement angle, the intermediate angle, the final measurement angle, all the intermediate measurement angles, and the average measurement angle is set and is added to or subtracted from the data of the transepidermal water loss.

Figure 6:
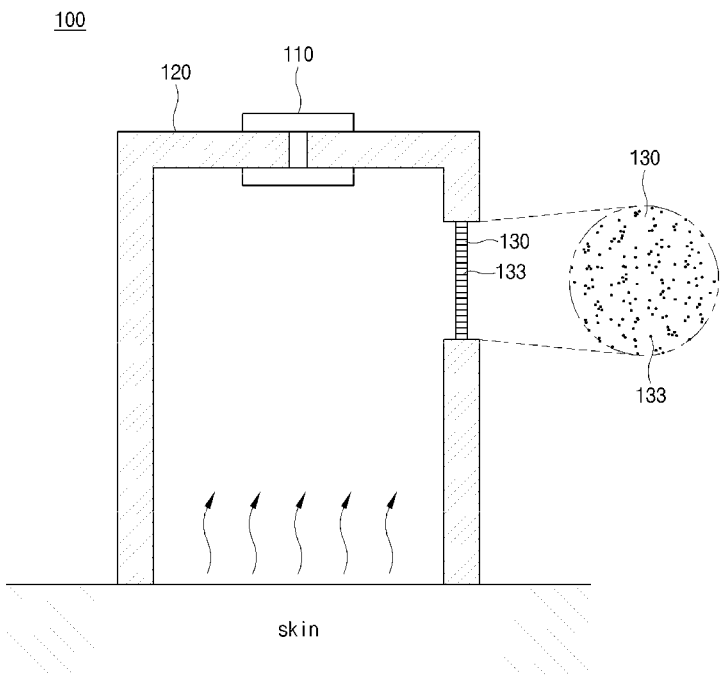
FIGS. 6 and 7 are cross-sectional views illustrating the configuration of the transepidermal water loss measurement device of FIG. 1.

FIG. 6 is a cross-sectional view illustrating the configuration of the transepidermal water loss measurement device of FIG. 1.

As illustrated in FIG. 6, at least a portion of the wall of the closed chamber of the transepidermal water loss measurement device 100 is provided with the pressure-adjusting ventilation unit 130. The pressure-adjusting ventilation unit 130 may vary in size or thickness.

For example, the pressure-adjusting ventilation unit 130 has a thin film shape that is thinner than the wall of the closed chamber 120. Preferably, the pressure-adjusting ventilation unit 130 is a ventilating functional thin film 133 that allows the air to pass, thereby relieving the internal pressure in the closed chamber but does not allow the vapor to pass.

When the pressure-adjusting ventilation unit 130 is implemented as the ventilating functional thin film 133 that allows the outflow of the internal air so that the internal pressure can be relieved but blocks the vapor, the pressure gradient and the density gradient can be adjusted according to the pressure difference and the density difference between the inside and the outside of the closed chamber 120.

Specifically, as described above, since the rate of increase in the partial pressure of the water vapor due to water evaporation from the skin surface and the transfer rate of the pressure in the closed chamber 120 are faster than the vapor diffusion and convection caused by the high skin temperature in the closed chamber 120, the air in the closed chamber 120 can be released into the atmosphere from the closed chamber 120 through the ventilating functional thin film 133. Therefore, the inside of the closed chamber 120 can be maintained at a constant pressure. Assuming that the temperature rise during the measurement of the transepidermal water loss is 1°, the volume increase and the pressure increase are each 0.33%. However, since the internal air is exhausted through the ventilating functional thin film 133, the inside of the closed chamber can be maintained at a constant pressure.

Figure 7:
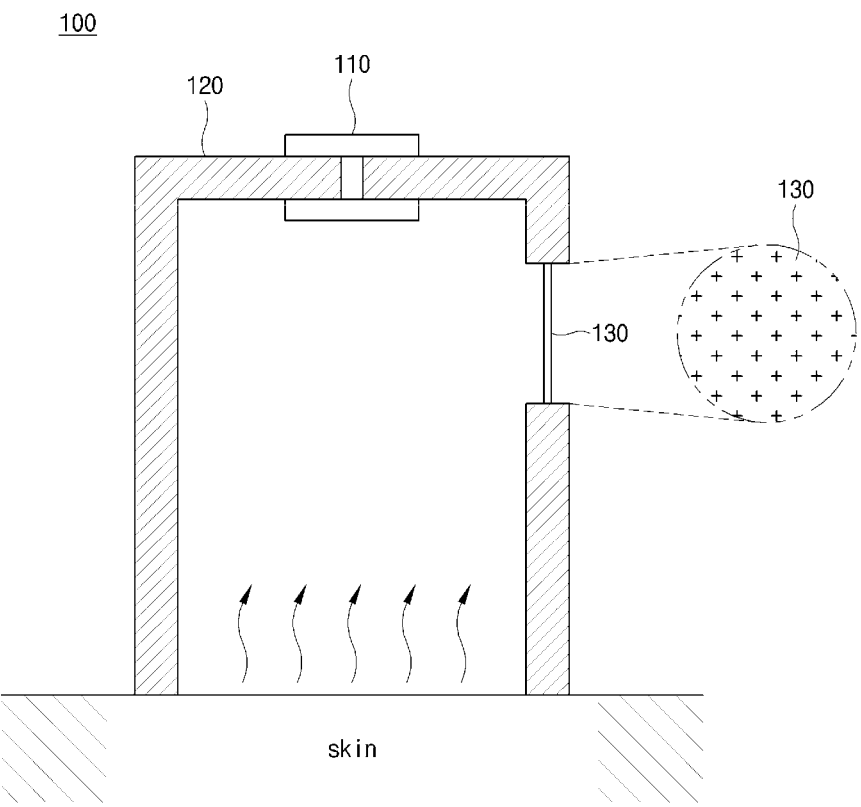

FIG. 7 is a cross-sectional view illustrating the configuration of the transepidermal water loss measurement device of FIG. 1.

As illustrated in FIG. 7, at least a portion of the wall of the closed chamber of the transepidermal water loss measurement device 100 is provided with the pressure-adjusting ventilation unit 130. The pressure-adjusting ventilation unit 130 may vary in size or thickness.

For example, the pressure-adjusting ventilation unit 130 is formed as a thin film thinner than the wall of the closed chamber 120, and is formed of a flexible thin film made from a flexible material such as silicone, rubber, or poly-series synthetic fiber.

When the pressure-adjusting ventilation unit 130 is implemented as a thin film made from a flexible material such as silicone, rubber, or poly-series synthetic fiber, the flexible thin film is stretched due to the pressure difference between the inside and the outside of the closed chamber 120. Therefore, the density and the pressure in the closed chamber 120 are reduced and the pressure gradient and the density gradient in the closed chamber can be adjusted.

Figure 8:
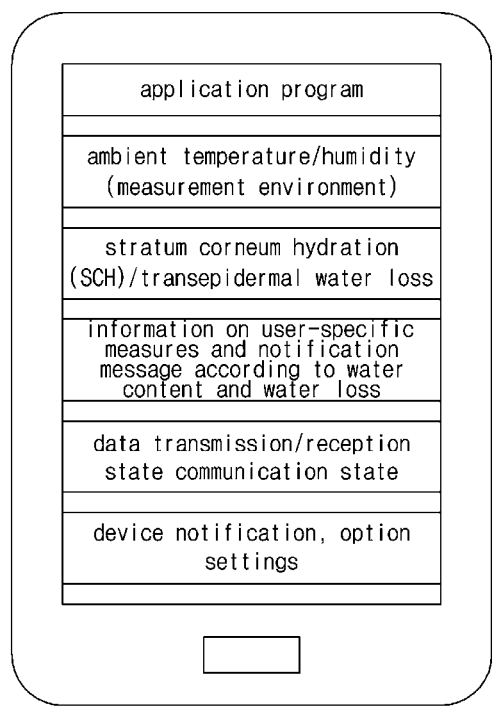
FIG. 8 is a diagram illustrating a screen displayed when an application program is executed in a mobile communication device of the skin care system of FIG. 1.

FIG. 8 is a diagram illustrating a screen displayed on the display unit of the mobile communication device when an application program is executed in the mobile communication device of the skin care system of FIG. 1.

Referring to 8, the mobile communication device 200 performs real-time short-range wireless communication with at least one transepidermal water loss measurement device 100 located adjacent to the mobile communication device 200, thereby receiving data of transepidermal water loss information in real time from at least one of the transepidermal water loss measurement devices 100.

The mobile communication device 200 provided with the data of the transepidermal water loss information numerically presents the data of the transepidermal water loss information using an application program executed therein to the user so that the user can recognize the transepidermal water loss information.

In addition, the mobile communication device may display information of the ambient temperature and the humidity during the measurement of the transepidermal water loss using the application program executed therein, receive a user-specific skin caring method and the related information according to the data of the transepidermal water loss information from the management server 300, and displays the received skin caring method and the related information.

Figure 9:
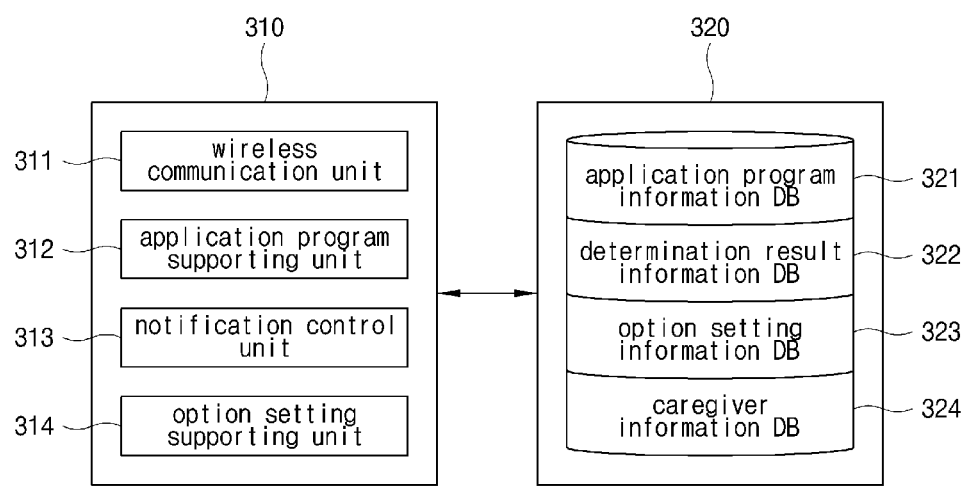
FIG. 9 is a block diagram illustrating the configuration of a management server of the skin care system of FIG. 1.

FIG. 9 is a block diagram illustrating the configuration of the management server of the skin care system of FIG. 1.

The management server 300 illustrated in FIG. 9 supports an application program that is executed in at least one mobile communication device 200 and provides information on option settings to the transepidermal water loss management device 100 and the mobile communication device 200 when the application program is executed. The management server 300 includes a notification information processing unit 310 and a database unit 320. The notification information processing unit 310 transmits the transepidermal water loss information to a certain registered mobile communication device 200 when receiving the transepidermal water loss information from a mobile communication device 200 that is different from the former mobile communication device 200. The database unit 320 stores personal information of each of the mobile communication devices 200 that are registered in association with unique numbers of the respective transepidermal water loss measurement devices 100 so that the personal information can be accessed and shared by the interested parties. The database unit 320 also manages personal information of registered caregivers via the application program executed in the mobile communication device.

The notification information processing unit 310 includes a wireless communication unit 311, an application program supporting unit 312, a notification control unit 313, and an option setting supporting unit 314.

The database unit 320 stores an application program information DB 321 to be provided to the application program supporting unit 312 to support the application program, a determination result information DB 322 storing the transepidermal water loss information in real time transmitted from a certain mobile communication device 200 and providing the transepidermal water loss information to the notification control unit 313, an option setting information DB 323 supporting option setting of the transepidermal water loss measurement device 100 and the mobile communication device 200, and a caregiver information DB 324 that stores and provides personal information of the owners of the mobile communication devices 200, which are registered in association with the unique numbers of the transepidermal water loss measurement devices 100, in association with the unique numbers of the transepidermal water loss measurement devices 100.

More specifically, the wireless communication unit 311 of the notification information processing unit 310 performs wireless communication based on long-range wireless Internet communication technology with at least one mobile communication device 200. The application program supporting unit 312 supports the application program executed in at least one mobile communication device 200 on the basis of the application program information DB 321.

Meanwhile, the notification control unit 313 stores the personal information of the mobile communication devices 200 corresponding to the respective transepidermal water loss measurement devices 100 in association with the unique numbers of the transepidermal water loss measurement devices 100. Since the personal information of the caregivers registered through the application program is managed, when the transepidermal water loss information is received from any of the mobile communication devices 200, the received transepidermal water loss information is transmitted to at least one mobile communication device of another registered caregiver so as to be shared. Accordingly, at least one caregiver at a remote location, who is provided with the transepidermal water loss information from the management server 300, can share the transepidermal water loss information of the user of the transepidermal water loss measurement device in real time.

As described above, the transepidermal water loss measurement device and the skin care system using the same can automatically correct measured values of transepidermal water loss according to an inclination at a specific time point within the measurement period or an average gradient over the measurement period and prevent a rapid change in measurement conditions such as the internal temperature and the density in the closed chamber, thereby improving the measurement accuracy and the reliability of the measured results of transepidermal water loss.

In addition, the transepidermal water loss measurement device and the user mobile communication device are configured to interwork with the management server to share accurate and reliable measurements (measured rates of water loss) and to effectively give information on skin care according to the measured results.

While the present invention has been described with reference to exemplary embodiments, it is to be understood by those skilled in the art that the present invention is not limited to the disclosed exemplary embodiments but rather various changes and modifications to the exemplary embodiments are possible without departing from the spirit and scope of the appended claims.

The invention claimed is:

1. A transepidermal water loss measurement device comprising:
   a cylindrical closed chamber with a closed end and an open end configured to come into contact with skin at a position at which a rate of transepidermal water loss is to be measured;
   a transepidermal water loss measurement analyzer configured to:
   measure the rate of transepidermal water loss by detecting a humidity and a humidity change in the closed chamber,
   detect the humidity and an inclination or measurement angle of the closed chamber when detecting the humidity, thereby correcting a measured value of the transepidermal water loss according to the inclination or measurement angle of the closed chamber,
   wherein the transepidermal water loss measurement analyzer is further configured to:
   detect the humidity and the humidity change in the closed chamber at fixed intervals of time during measurement of the transepidermal water loss and to analyze the detected humidity and the detected humidity changes to calculate the transepidermal water loss;
   detect in real time the inclination or measurement angle of the closed chamber at the fixed intervals of time when detecting the humidity using at least one acceleration sensor, gyro sensor, or water droplet sensor; and
   correct the measured value of the transepidermal water loss according to the detected inclination or measurement angles of the cylindrical closed chamber at the fixed intervals of time.

2. The transepidermal water loss measurement device according to claim 1, wherein the transepidermal water loss measurement device comprises:
   a water content sensing unit including at least one humidity sensor or at least one moisture sensor, the at least one humidity sensor or the at least one moisture sensor configured to detect the humidity in the closed chamber at the fixed intervals of time during the measurement of the transepidermal water loss; and
   wherein the transepidermal water loss measurement analyzer is further configured to receive the humidity detected by the water content sensing unit in real time and to analyze the humidity and the humidity change at the fixed intervals of time, thereby calculating the transepidermal water loss.

3. The transepidermal water loss measurement device according to claim 2, wherein, with respect to the measured rate of transepidermal water loss, a predetermined threshold value corresponding to at least one of the detected inclination or measurement angles of the closed chamber at the fixed intervals of time including an initial measurement angle, an intermediate measurement angle, a final measurement angle, all intermediate measurement angles during a measurement period, and an average measurement angle during the measurement period is set, or the predetermined threshold value is added to or subtracted from the measured rate of transepidermal water loss, thereby correcting numerical values of the transepidermal water loss.

4. The transepidermal water loss measurement device according to claim 1, wherein the transepidermal water loss measurement analyzer is configured to detect angle information including at least one of an initial measurement angle, an intermediate measurement angle, a final measurement angle, all intermediate measurement angles during a measurement period, and an average measurement angle during the measurement period when measuring the transepidermal water loss amount; sets a predetermined threshold value corresponding to at least one of the initial measurement angle, the intermediate measurement angle, the final measurement angle, all the intermediate measurement angles, and the average measurement angle, with respect to data of the transepidermal water loss; or adds or subtracts the predetermined threshold value, thereby correcting numerical data of the transepidermal water loss.

5. The transepidermal water loss measurement device according to claim 1, wherein the transepidermal water loss measurement analyzer is configured to determine whether or not the closed chamber is moved by a predetermined reference angle or more during a measurement period in which the humidity changes are measured; requests repeating a process of measuring and analyzing the humidity changes when it is determined that the closed chamber is moved by the predetermined reference angle or more such that the transepidermal water loss, an initial measurement angle, an intermediate measurement angle, a final measurement angle, all intermediate measurement angles during the measurement period, and an average measurement angle during the measurement period are measured again; and corrects numerical data of the transepidermal water loss when it is determined that the closed chamber is moved by less than the predetermined reference angle by setting a predetermined threshold value corresponding to at least one of the initial measurement angle, the intermediate measurement angle, the final measurement angle, all the intermediate measurement angles, and the average measurement angle, or by adding or subtracting the predetermined threshold value.

6. The transepidermal water loss measurement device according to claim 1, wherein the closed chamber is provided with a pressure-adjusting ventilation unit having a predetermined area and a predetermined thickness on an outer surface of a wall of the closed chamber, the pressure-adjusting ventilation unit functioning to adjust a pressure gradient and a density gradient inside the closed chamber in accordance with a pressure difference and a density difference between an inside space and an outside space of the closed chamber.

7. The transepidermal water loss measurement device according to claim 6, wherein the pressure-adjusting ventilation unit has a thin film shape having a thickness equal to or smaller than that of the wall of the closed chamber and is provided with multiple ventilation holes that are arranged regularly or irregularly and have an inner diameter that is $1/1000$ times a total surface area of the closed chamber or a total surface area of the pressure-adjusting ventilation unit.

8. The transepidermal water loss measurement device according to claim 6, wherein the pressure-adjusting ventilation unit has a thin film shape thinner than the wall of the closed chamber and is implemented as a ventilating functional thin film that allows outflow of internal air and prevents outflow of vapor therethrough.

9. The transepidermal water loss measurement device according to claim 6, wherein the pressure-adjusting ventilation unit has a thin film shape thinner than the wall of the closed chamber and is implemented as a flexible thin film made from at least one of silicon, rubber, or poly-series synthetic fiber.

10. The transepidermal water loss measurement device according to claim 6, wherein the transepidermal water loss measurement analyzer is configured to measure the transepidermal water loss by detecting the humidity in the closed chamber, display data of the measured transepidermal water loss on a display unit, and transmit the data of the measured transepidermal water loss to an external device through a wireless communication network.

11. The transepidermal water loss measurement device according to claim 10, wherein the transepidermal water loss measurement analyzer is further configured to:

detect the humidity in the closed chamber, calculate the transepidermal water loss from the detected humidity by analyzing the humidity and the humidity changes measured at the fixed intervals of time and generate data of the transepidermal water loss, wherein the transepidermal water loss measurement device further comprises:

a display unit displaying a numerical value of the data of the calculated transepidermal water loss; and a communication unit transmitting the data of the calculated transepidermal water loss through the wireless communication network to the external device such that the data of the transepidermal water loss is shared.

12. A skin care system using a transepidermal water loss measurement device, the system comprising:

one or more transepidermal water loss measurement devices according to claim 1; and one or more mobile communication devices that receive the rate of the transepidermal water loss from at least one of the transepidermal water loss measurement devices through a short-range wireless communication network and displays the data of the transepidermal water loss in a numerical value form by using an application program, thereby allowing a user to recognize information of the transepidermal water loss.

13. The skin care system according to claim 12, further comprising a management server supporting the application program executed in the one or more mobile communication devices, providing the rate of the transepidermal water loss received from one of the mobile communication devices to another mobile communication device, and providing a user-specific skin caring method and related information on the basis of the rate of the transepidermal water loss.

* * * * *